United States Patent [19]

Yabe

[11] Patent Number: 4,757,805
[45] Date of Patent: Jul. 19, 1988

[54] ENDOSCOPE
[75] Inventor: Hisao Yabe, Tokyo, Japan
[73] Assignee: Olympus Optical Co., Ltd., Japan
[21] Appl. No.: 63,234
[22] Filed: Jun. 17, 1987
[30] Foreign Application Priority Data Jun. 25, 1986 [JP] Japan ................................ 51-148618

[51] Int. Cl.[4] ............................................. A61B 1/04
[52] U.S. Cl. .......................................... 128/6; 358/98
[58] Field of Search .......................... 128/4, 6; 358/98

[56] References Cited

U.S. PATENT DOCUMENTS

| 4,573,450 | 3/1986 | Arakawa | 128/6 |
|---|---|---|---|
| 4,622,954 | 11/1986 | Arakawa et al. | 128/6 |
| 4,641,635 | 2/1987 | Yabe | 128/6 |
| 4,646,721 | 3/1987 | Arakawa | 128/6 |
| 4,646,723 | 3/1987 | Arakawa | 128/6 |
| 4,667,656 | 5/1987 | Yabe | 128/6 |
| 4,682,219 | 7/1987 | Arakawa | 358/98 |
| 4,692,608 | 9/1987 | Cooper et al. | 128/6 X |
| 4,697,210 | 9/1987 | Toyota et al. | 358/98 |

FOREIGN PATENT DOCUMENTS 60-241010 11/1985 Japan .

Primary Examiner—William H. Grieb

[57] ABSTRACT

An endoscope according to the present invention comprises an insertion section which as a distal structure. An objective optical system is disposed in the distal structure so as to be substantially parallel to the longitudinal axis thereof. A solid-state image sensing device, which has a light receiving surface with an image area therein, is disposed in the distal structure, so as to be substantially parallel to a plane which contains the longitudinal axis of the distal structure. An optical element is attached to an end portion of the objective optical system, whereby the optical path of a light incident on the objective optical system is bent substantially at right angles, so that the light is guided to the light receiving surface of the image sensing device. The endoscope further comprises a forceps channel having one end attached to the distal structure. The longitudinal axis of the forceps channel is situated on a plane which contains the longitudinal axis of the objective optical system and extends substantially parallel to the light receiving surface of the image sensing device. Thus, the distal structure of the insertion section can be made thinner.

9 Claims, 4 Drawing Sheets

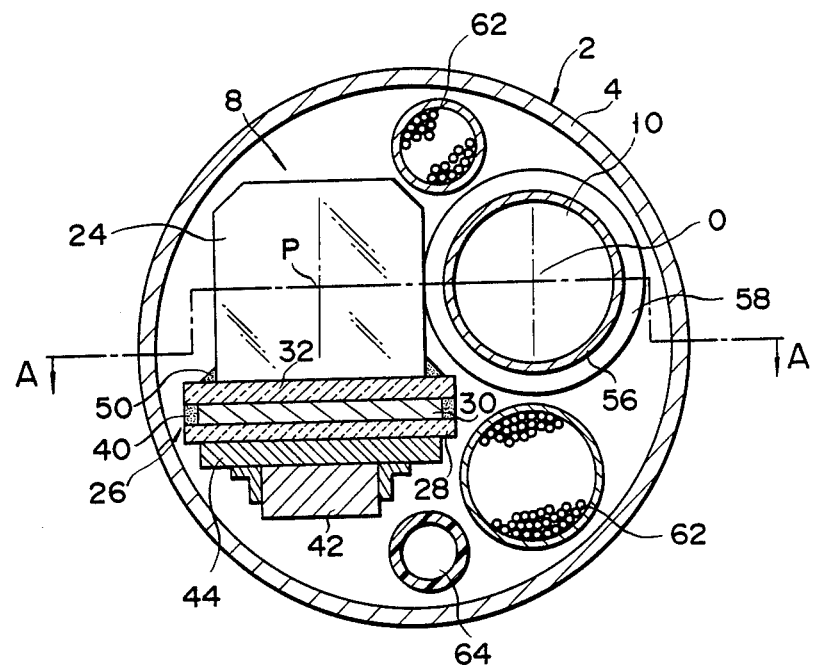
F I G. 1

ENDOSCOPE

BACKGROUND OF THE INVENTION

A. Field of the Invention

The present invention relates to an endoscope having a distal structure fitted with a solid-state image sensing device, such as an SID.

B. Description of the Prior Art

Among prior art endoscopes adapted for observation in a body cavity, an improved endoscope is disclosed in Japanese Patent Disclosure (Kokai) No. 60-241010, for example. This endoscope has a distal structure which is fitted with a solid-state image sensing device, such as an SID.

In such a conventional endoscope, the image sensing device is situated on a plane which contains the longitudinal axis of the distal structure of an insertion section. An objective optical system is disposed in one of the upper and lower spaces of the image sensing device, while a forceps channel is located in the other. A prism is attached to an end portion of the optical system. It serves to totally reflect a light incident on the optical system, at right angles, thereby guiding the light to the image sensing device.

In the endoscope whose solid-state image sensing device is situated on the plane containing the longitudinal axis of the distal structure, as described above, the objective optical system, a light guide, the forceps channel, and an air-water feed channel must be housed within a space which is restricted to the upper and lower portions of the image sensing device. However, the space inside the distal structure is limited, depending on the heights of the optical system and the prism, the thicknesses of the image sensing device and a substrate, the thicknesses of various channels, and the locations of the various members. If a relatively thick forceps channel is to be disposed in the limited space, the outside diameter of the distal structure must be increased.

Thus, in conventional endoscopes, the arrangement of a relatively thick forceps channel in the insertion section, for the use of various medical instruments, is not compatible with the use of a thinner distal structure of the insertion section, which is required to avoid excessive pain for the patient.

SUMMARY OF THE INVENTION

The object of the present invention is to provide an endoscope which can be provided with a forceps channel of a relatively large diameter, without increasing the outside diameter of its distal structure.

The above object is achieved by an endoscope constructed as follows. The endoscope comprises an insertion section which has a distal structure. An objective optical system is disposed in the distal structure so as to be substantially parallel to the longitudinal axis thereof. A solid-state image sensing device, which has a light receiving surface with an image area therein, is disposed in the distal structure, so as to be substantially parallel to a plane which contains the longitudinal axis of the distal structure. An optical element is attached to an end portion of the objective optical system, whereby the optical path of the light incident on the objective optical system is bent substantially at right angles, so that the light is guided to the light receiving surface of the image sensing device. The endoscope further comprises a forceps channel having one end attached to the distal structure. The longitudinal axis of the forceps channel is situated on a plane which contains the longitudinal axis of the objective optical system and extends substantially parallel to the light receiving surface of the image sensing device.

Thus, in the endoscope according to the invention, the distal structure of the insertion section can be made thinner than that of a typical endoscope whose solid-state image sensing device is disposed between an objective optical system and a forceps channel. Accordingly, the patient can experience less pain while the insertion section is being inserted in the body cavity. Also, a forceps channel having a relatively large outside diameter can be located in the insertion section.

BRIEF DESCRIPTION OF THE DRAWINGS

FIG. 1 is a cross-sectional view showing a distal structure of an insertion section of an endoscope according to a first embodiment of the present invention;

DETAILED DESCRIPTION OF THE PREFERRED EMBODIMENTS

Preferred embodiments of the present invention will now be described with reference to the accompanying drawings.

Figure 2:
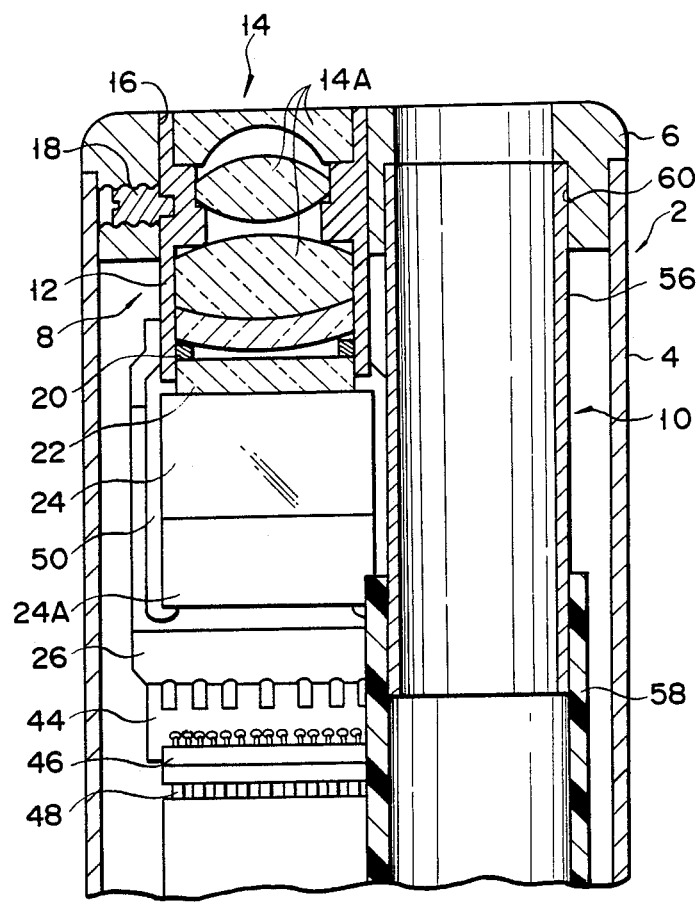
FIG. 2 is a sectional view of the distal structure taken along line A—A of FIG. 1.

FIGS. 1 and 2 show an endoscope according to a first embodiment of the present invention. As shown in FIG. 2, the endoscope comprises an insertion section which has distal structure 2. Structure 2 includes distal cylinder 4 and distal member 6 fitted in the distal end of cylinder 4. Image sensing unit 8 and forceps channel 10 are arranged inside cylinder 4.

Image sensing unit 8 will now be described in detail. Unit 8 comprises lens group 14A, constituting objective optical system 14, and lens frame 12 for supporting the lens group. Frame 12 is fitted in mounting hole 16 in distal member 6, and is fixed by means of fixing screw 18. Filter 22 is attached to the rear end portion of lens frame 12 with the aid of spacer 20. Prism 24, for use as an optical element, is attached to the rear face of filter 22. Prism 24 serves to totally reflect an incident light from optical system 14 substantially at right angles. Solid-state image sensing device 26, such as an SID, is disposed on the optical axis of the reflected light from prism 24. Device 26 having a light receiving surface 51 is positioned substantially parallel to a plane which contains the longitudinal axis of distal structure 2.

Figures 3, 4, 5:
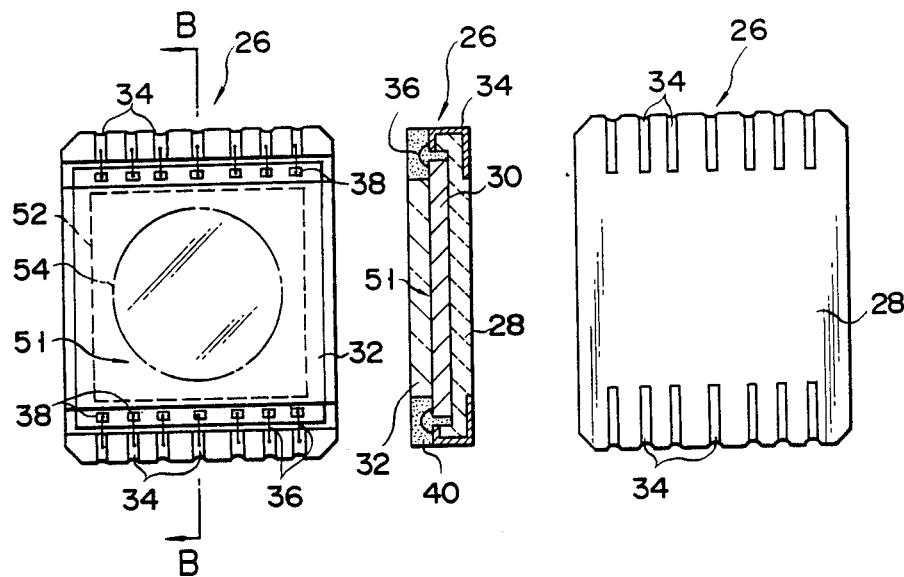
FIG. 3 is a plan view showing a solid-state image sensing device according to the first embodiment.
FIG. 4 is a sectional view of the image sensing device taken along line B—B of FIG. 3.
FIG. 5 is a bottom view of the image sensing device shown in FIG. 3.

As shown in FIGS. 3, 4 and 5, solid-state image sensing device 26 has ceramic base 28. SID chip 30 and color filter array 32 are bonded to base 28. A number of leads 34 are arranged crosswise at predetermined intervals, along each of two opposite edge portions of the upper and lower surfaces of base 28. Leads 34 are bonded individually to bonding pads 38 of SID chip 30 by means of bonding wires 36. As shown in FIG. 4, each lead 34 is insulated by bonding agent 40, which is used to bond filter array 32 to chip 30 and base 28. Wires 36 may alternatively be interposed between base 28 and chip 30. As shown in FIGS. 1 and 2, moreover, ceramic base 28 of solid-state image sensing device 26 is fixed to the upper surface of printed board 44, on which electrical component 42 is mounted. Board 44 is connected electrically to cable 48 by means of connector 46. Color filter array 32 of image sensing device 26 is fixed to prism 24 by means of bonding agent 50.

As shown in FIG. 3, image sensing device 26 has square image area 52, and a circular image is displayed on a monitor by utilizing circular central region 54. Even if any other part adjacent to device 26 overlaps image area 52 to some extent, therefore, it cannot influence the displayed image on the monitor. If circular region 54 is utilized, the number of pixels used to detect the image is reduced. Thus, working region 54 may be enlarged for such a fiberscope as a rectoromanoscope in which distal structure 2 can have a relatively large diameter.

By using solid-state image sensing device 26 having the square image area, as described above, the size of working region 54 can be changed depending on the type of the fiberscope used. The image sensing device according to the first embodiment has 480 pixels with respect to each of vertical and horizontal lines. Out of each 480 pixels, 400 are used for the diameter of region 54. The display section of an NTSC (National Television System Committee) TV monitor has about 440 vertical scanning lines, so that the region of the image area for 40 scanning lines can be utilized as a character information area. The TV monitor used should have a horizontal resolution of 600 lines or more.

As shown in FIG. 2, forceps channel 10 includes channel pipe 56 and channel tube 58. The distal end portion of pipe 56 is fixedly fitted in mounting hole 60 in distal member 6, and tube 58 is connected to the proximal end portion of pipe 56. As shown in FIG. 1, longitudinal axes P and 0 of objective optical system 14 of image sensing unit 8 and channel 10 are situated on a plane which is substantially parallel to light receiving surface 51 of solid-state image sensing device 26. Accordingly, even though forceps channel 10 is located close to optical system 14, channel pipe 56, which is smaller in outside diameter than any other portions of channel 10, adjoins system 14, and the distal end portion of channel tube 58 is situated within a space over slanting face 24A of prism 24, i.e., that portion of prism 24 which is situated relatively low above image sensing device 26. Thus, prism 24 and tube 58 cannot overlap each other on the same plane, so that system 14 and channel 10 can be brought close to each other. Accordingly, the outside diameter of distal structure can be reduced. Light guide 62 and air-water feed tube 64 are arranged parallel to channel 10, in a space inside structure 2.

Figure 6:
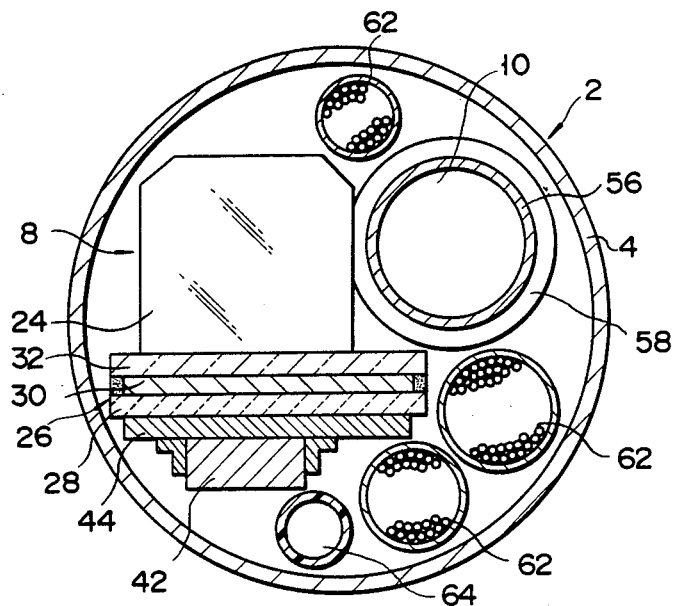
FIG. 6 is a cross-sectional view showing a distal structure of an insertion section of an endoscope according to a second embodiment of the invention.
Figure 7:
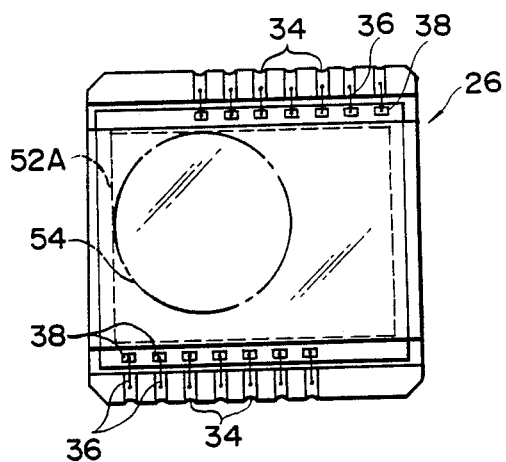
FIG. 7 is a plan view showing a solid-state image sensing device according to the second embodiment.

FIGS. 6 and 7 show an endoscope according to a second embodiment of the present invention. In this embodiment, solid-state image sensing device 26 has image area 52A whose length-to-width ratio is 3 : 4. Also, device 26 has 480 and 640 pixels with respect to the vertical and horizontal directions, respectively. Constructed in this manner, device 26 can be used in a non-professional, home-type TV camera, so that it can be manufactured at low cost by the effect of mass production. When using device 26 for household use, only the SID chip may be produced without assembling the image sensing device into a medical package. In this case, SID chip 30 can be utilized for household use, thus enhancing the effect of mass production.

In the second embodiment, moreover, working region 54 of image area 52A is a circular region which includes 400 pixels for its diameter. As shown in FIG. 7, region 54 is secured at the upper-left portion of area 52A. As shown in FIG. 6, therefore, prism 24 is situated at one side, that is, at the left-side portion of solid-state image sensing device 26. Thus, a wide space can be secured in the right-side portion of distal cylinder 4. In the second embodiment, as described above, region 54 is situated at the upper-left portion of area 52A. Alternatively, however, it may be situated at the upper- or lower-right portion of area 52A, depending on the locations of various built-in members of endoscopes of various types, such as side-view scopes or those endoscopes having two forceps channels.

In the second embodiment, furthermore, leads 34 of image sensing device 26 are arranged along both edge portions of distal structure 2, in the longitudinal direction thereof. Alternatively, however, the leads may be arranged along the edge portions of structure 2 extending at right angles to the longitudinal axis thereof.

Thus, the outside diameter of distal structure 2 can be reduced further by suitably adjusting the mounting direction of solid-state image sensing device 26 or the working region in image area 52A.

Figure 8:
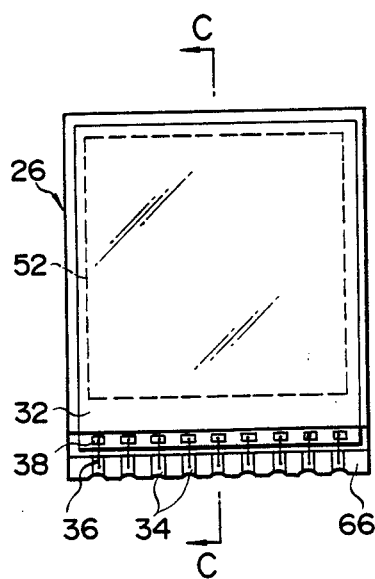
FIG. 8 is a plan view showing a solid-state image sensing device according to a third embodiment of the invention.
Figures 9, 10:
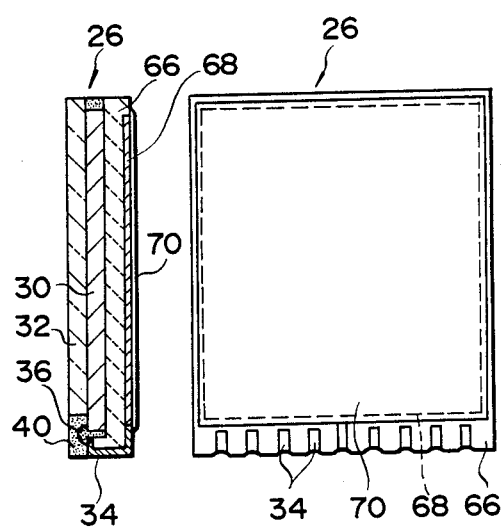
FIG. 9 is a sectional view of the image sensing device taken along line C—C of FIG. 8.
FIG. 10 is a bottom view of the image sensing device shown in FIG. 8.

FIGS. 8, 9 and 10 show solid-state image sensing device 26 according to a third embodiment of the present invention. In the foregoing embodiments, ceramic base 28 is used in device 26. In the third embodiment, on the other hand, device 26 includes glass-epoxy base 66. Earth board 68 is attached to the back of base 66. It serves to stabilize the reference potential of SID chip 30 and remove noise. Earth board 68 is covered with resist 70. Image area 52 of device 26 is a square area having 400×400 pixels. Leads 34 are arranged in a line on one edge portion of base 66, which is located closer to the operating section of the endoscope, with respect to the longitudinal axis of distal cylinder 4. Thus, according to the third embodiment, printed board 44 and connector 46 can be connected more quickly.

Also in the first and second embodiments wherein ceramic base 28 is used, leads 34 can be arranged in a line on one edge portion of ceramic base 28. In this case, too, the same advantage can be attained as in the third embodiment.

What is claimed is:

1. An endoscope with an insertion section having a distal structure, comprising:
   an objective optical system disposed in the distal structure so as to be substantially parallel to the longitudinal axis thereof;
   a solid-state image sensing device disposed in the distal structure so as to be substantially parallel to a plane containing the longitudinal axis of the distal structure, said image sensing device having a light receiving surface with an image area therein;

an optical element attached to an end portion of the objective optical system, and adapted to bend the optical path of a light incident on the objective optical system substantially at right angles, thereby guiding the light to the light receiving surface of the image sensing device; and a forceps channel having one end attached to the distal structure, the longitudinal axis of said forceps channel being situated on a plane containing the longitudinal axis of the objective optical system and extending substantially parallel to the light receiving surface of the image sensing device.

2. The endoscope according to claim 1, wherein said optical element is a prism.

3. The endoscope according to claim 1, wherein said solid-state image sensing device has a square image area, and said optical element is situated in the center of the image area.

4. The endoscope according to claim 1, wherein said solid-state image sensing device has an image area whose longitudinal and transverse lengths are different.

5. The endoscope according to claim 4, wherein the ratio of the longitudinal length of the image area to the transverse length thereof is 3 : 4.

6. The endoscope according to claim 4, wherein said optical element is located such that its center is to one side of, and does not coincide with, the center of the image area of the solid-state image sensing device.

7. The endoscope according to claim 1, wherein said solid-state image sensing device includes a ceramic base.

8. The endoscope according to claim 1, wherein said solid-state image sensing device includes a glass-epoxy base.

9. The endoscope according to claim 8, wherein said glass-epoxy base has lead means only on one sideedge portion thereof.

* * * * *